United States Patent [19]

Kukla

[11] 4,137,414
[45] Jan. 30, 1979

[54] 5-SUBSTITUTED-2-PHENYLBENZO[b]THIOPHENE-3-ALKYLAMINES AND RELATED COMPOUNDS

[75] Inventor: Michael J. Kukla, Skokie, Ill.

[73] Assignee: G. D. Searle & Co., Chicago, Ill.

[21] Appl. No.: 836,868

[22] Filed: Sep. 26, 1977

[51] Int. Cl.$^2$ .................... C07D 333/58; C07D 409/06
[52] U.S. Cl. ........................ 544/376; 260/326.5 SA;
260/326.84; 260/330.5
[58] Field of Search ............... 260/268 BC, 326.84,
260/330.5, 326.5 SA; 544/376

[56] References Cited

U.S. PATENT DOCUMENTS

| | | | |
|---|---|---|---|
| 3,070,606 | 12/1962 | Anderson | 260/326.84 |
| 3,594,478 | 7/1971 | Brandstrom et al. | 260/330.5 |
| 3,910,955 | 10/1975 | Chapman et al. | 260/330.5 |
| 3,947,470 | 3/1976 | Brenner et al. | 260/330.5 |

OTHER PUBLICATIONS

Descamps et al, *Chim. Ther.*, vol. 8 (1973), pp. 536–544.

*Primary Examiner*—Paul M. Coughlan, Jr.
*Attorney, Agent, or Firm*—Joy A. Serauskas

[57] ABSTRACT

The invention encompasses novel 5-substituted-2-phenylbenzo[b]thiophene-3-alkylamines and related compounds of the general formula

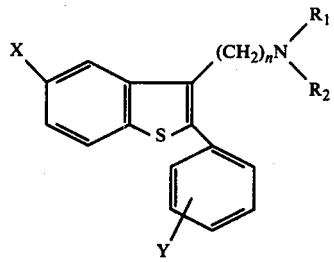

and the pharmaceutically acceptable acid addition salts thereof wherein $R_1$ and $R_2$ each independently represents H or an alkyl having from 1 to 8 carbon atoms or $R_1$ and $R_2$ together with N represents an azamonocyclic ring selected from the group comprising pyrrolidinyl, piperazinyl, substituted pyrrolidinyl wherein the substituent is an alkyl containing from 1 to 4 carbon atoms and substituted piperazinyl wherein the substituent is an alkyl containing from 1 to 4 carbon atoms or an alkanol wherein the alkyl moiety contains 1 to 4 carbon atoms; Y represents H, halogen or alkyl having 1 to 4 carbon atoms; X represents H, halogen, alkyl having 1 to 4 carbon atoms and alkoxy wherein the alkyl moiety contains 1 to 4 carbon atoms; and n is a positive integer from 1 to 4. These compounds possess utility as neuroleptics or anti-bacterial agents.

21 Claims, No Drawings

5-SUBSTITUTED-2-PHENYLBENZO[b]THIOPHENE-3-ALKYLAMINES AND RELATED COMPOUNDS

The present invention encompasses novel 5-substituted-2-phenylbenzo[b]thiophene-3alkylamines and related compounds of the general formula

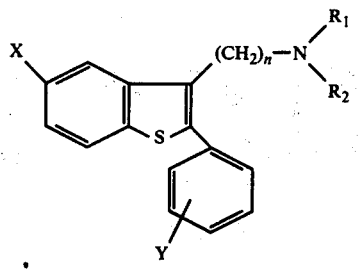

and the pharmaceutically acceptable acid addition salts thereof wherein $R_1$ and $R_2$ each independently represents H or alkyl having from 1 to 8 carbon atoms or $R_1$ and $R_2$ together with N represents an azamonocyclic ring selected from the group comprising pyrrolidinyl, piperazinyl, substituted pyrrolidinyl wherein the substituent is an alkyl containing from 1 to 4 carbon atoms and substituted piperazinyl wherein the substituent is an alkyl containing from 1 to 4 carbon atoms or an alkanol wherein the alkyl moiety contains 1 to 4 carbon atoms; Y represents H, halogen and alkyl having 1 to 4 carbon atoms; X represents H, halogen, alkyl having 1 to 4 carbon atoms and alkoxy wherein the alkyl moiety contains 1 to 4 carbon atoms; and n is a positive integer from 1 to 4.

The alkyl radicals are exemplified by methyl, ethyl, propyl, butyl, pentyl, hexyl, heptyl, and octyl and the corresponding branched chain isomers thereof.

The alkanols are exemplified by methanol, ethanol, propanol and butanol.

The alkoxys are exemplified by methoxy, ethoxy, propoxy and butoxy.

The halogens are exemplified by chloro, bromo, fluoro and iodo.

Preferred embodiments of the present invention as set out in formula I and the pharmaceutically acceptable acid addition salts thereof are those in which $R_1$ and $R_2$ each independently represent H or alkyl having from 1 to 8 carbon atoms; X represents H or halogen; Y represents H; and n is a positive integer from 1 to 4. Specifically 5-chloro-2-phenylbenzo[b]thiophene-3-ethanamine, hydrochloride; 5-chloro-2-phenylbenzo[b]thiophene-3-N,N-dimethylethanamine, hydrochloride; 5-chloro-2-phenylbenzo[b]thiophene-3-N,N-dimethylpropanamine, hydrochloride; 5-fluoro-2-phenylbenzo[b]thiophene-3-ethanamine, hydrochloride; 5-chloro-2-phenylbenzo[b]thiophene-3-N,N-dibutylethanamine, hydrochloride; 5-fluoro-2-phenylbenzo[b]thiophene-3-N,N-dimethylethanamine, hydrochloride; 2-phenylbenzo[b]-thiophene-3-N,N-dimethylethanamine, hydrochloride; 2-phenylbenzo[b]thiophene-3-ethanamine, hydrochloride; 5-chloro-2-phenylbenzo[b]thiophene-3-N,N-diethylethanamine, hydrochloride; 5-chloro-2-phenylbenzo[b]thiophene-3-N-methylethanamine, hydrochloride; 5-chloro-2-phenylbenzo[b]-thiophene-N,N-dimethylmethanamine; and 2-phenylbenzo[b]-thiophene-N,N-dimethylmethanamine, hydrochloride are preferred.

Preferred embodiments of the present invention as set out in formula I and the pharmaceutically acceptable acid addition salts thereof are those in which $R_1$ and $R_2$ together with N represents an azamonocyclic ring selected from the group comprising pyrrolidinyl, piperazinyl, substituted pyrrolidinyl wherein the substituent is an alkyl containing from 1 to 4 carbon atoms and substituted piperazinyl wherein the substituent is an alkyl containing from 1 to 4 carbon atoms or an alkanol wherein the alkyl moiety contains 1 to 4 carbon atoms; X represents H or halogen; Y represents H and n is a positive integer from 1 to 4. Specifically 1-[2-(5-chloro-2-phenylbenzo[b]-thiophen-3-yl)ethyl]-4-methylpiperazine, dihydrochloride; 1-[1-(5-chloro-2phenylbenzo[b]thiophen-3-yl)methyl]-4-ethanol piperazine, dihydrochloride; 1-[1-(5-chloro-2-phenylbenzo[b]thiophen-3-yl)methyl]-4-methylpiperazine, dihydrochloride; 1-[2-(5-chloro-2-phenylbenzo[b]thiophene-3-yl)ethyl]pyrrolidine, hydrochloride; and 1-[3-(5-chloro-2-phenylbenzo[b]thiophene-3-yl)propyl]-4-methylpiperazine, dihydrochloride are preferred.

The organic bases of this invention form non-toxic, acid-addition salts with a variety of organic and inorganic acids. Such salts are formed with acids such as sulfuric, phosphoric, hydrochloric, hydrobromic, hydroiodic, sulfamic, citric, lactic, maleic, malic, succinic, tartaric, cinnamic, acetic, benzoic, gluconic, ascorbic and related acids.

Scheme A

The compounds of the present invention as set out in formula I in which $R_1$ and $R_2$ each independently represent H or methyl; Y represents H, halogen, or alkyl having 1 to 4 carbon atoms; X represents H, halogen, alkyl having 1 to 4 carbon atoms, or alkoxy wherein the alkyl moiety contains 1 to 4 carbon atoms; and n is the positive integer 2 are generally prepared by the reaction sequence set out in Scheme A.

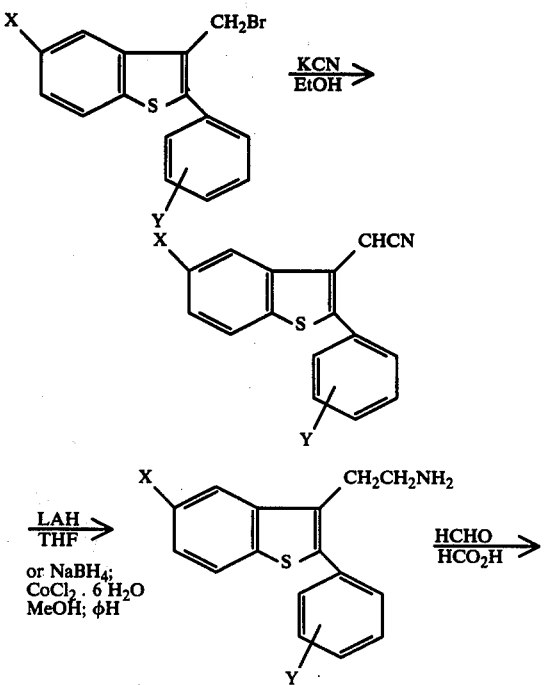

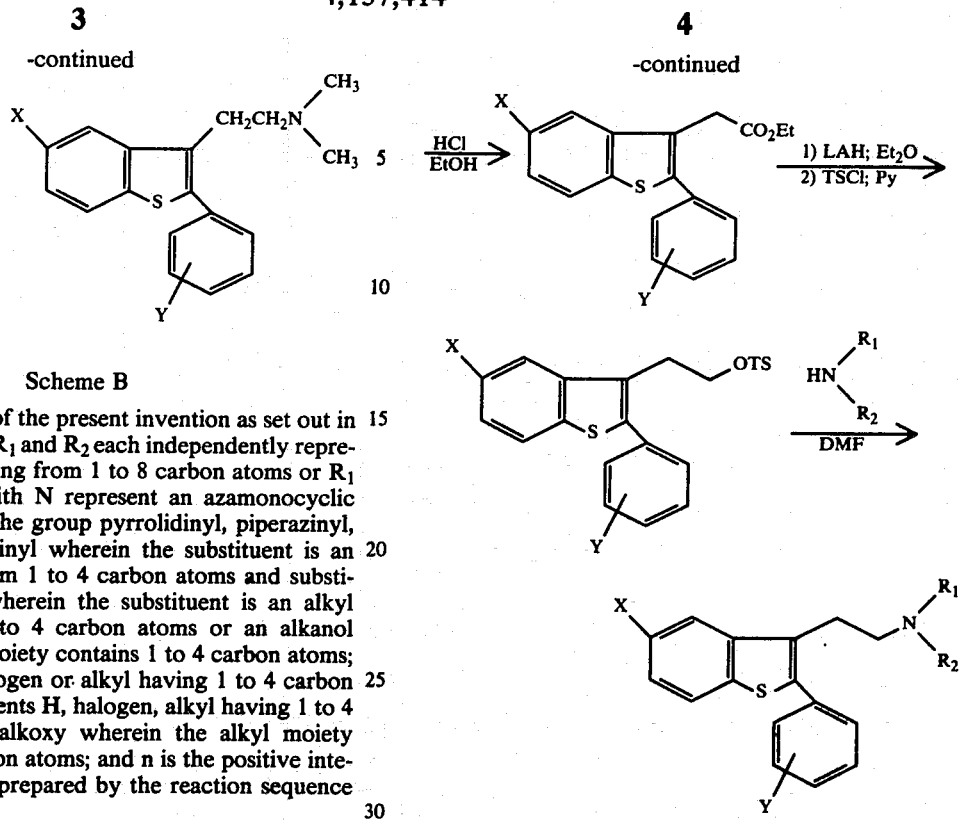

Scheme B

The compounds of the present invention as set out in formula I in which $R_1$ and $R_2$ each independently represent H or alkyl having from 1 to 8 carbon atoms or $R_1$ and $R_2$ together with N represent an azamonocyclic ring selected from the group pyrrolidinyl, piperazinyl, substituted pyrrolidinyl wherein the substituent is an alkyl containing from 1 to 4 carbon atoms and substituted piperazinyl wherein the substituent is an alkyl containing from 1 to 4 carbon atoms or an alkanol wherein the alkyl moiety contains 1 to 4 carbon atoms; Y represents H, halogen or alkyl having 1 to 4 carbon atoms; and X represents H, halogen, alkyl having 1 to 4 carbon atoms and alkoxy wherein the alkyl moiety contains 1 to 4 carbon atoms; and n is the positive integer 2 are generally prepared by the reaction sequence set out in Scheme B

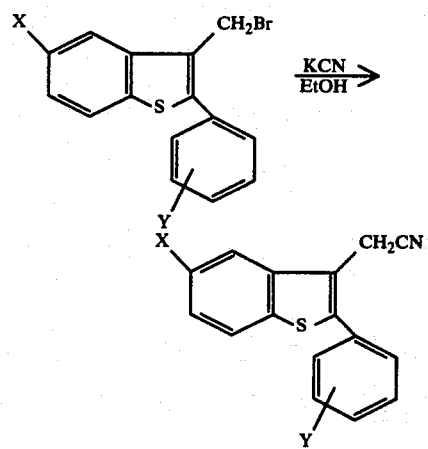

Scheme C

The compounds of the present invention as set out in formula I in which $R_1$ and $R_2$ each independently represent H or alkyl having from 1 to 8 carbon atoms or $R_1$ and $R_2$ together with N represent an azamonocyclic ring selected from the group pyrrolidinyl, piperazinyl, substituted pyrrolidinyl wherein the substituent is an alkyl containing from 1 to 4 carbon atoms and substituted piperazinyl wherein the substituent is an alkyl containing from 1 to 4 carbon atoms or an alkanol wherein the alkyl moiety contains 1 to 4 carbon atoms; Y represents H, halogen or alkyl having 1 to 4 carbon atoms, and X represents H, halogen, alkyl having 1 to 4 carbon atoms and alkoxy wherein the alkyl moiety contains 1 to 4 carbon atoms; and n is the positive integer 3 are generally prepared by the reaction sequence set out in Scheme C

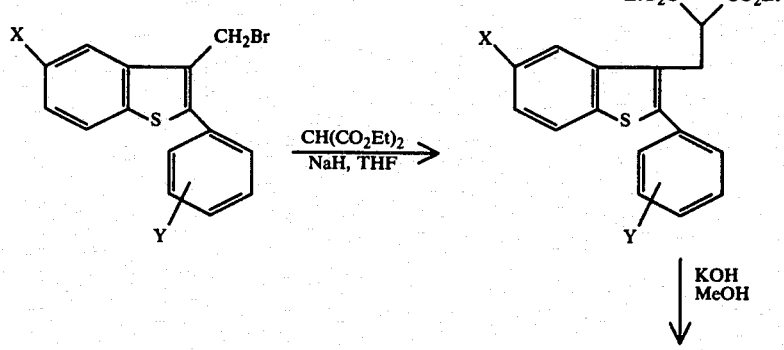

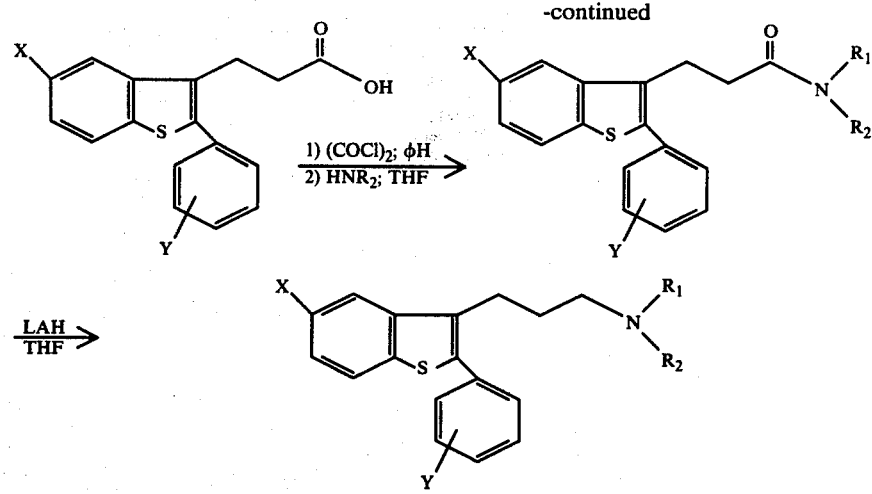

Substitution of the compound of the general formula

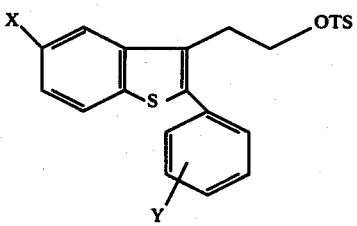

for the compound of the general formula

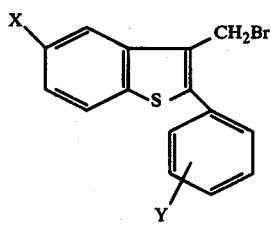

of Scheme C and repetition of the procedure which is outlined in Scheme C affords compounds of the present invention in which $R_1$ and $R_2$ each independently represent H or alkyl having from 1 to 8 carbon atoms or $R_1$ and $R_2$ together with N represent an azamonocyclic ring selected from the group pyrrolidinyl, piperazinyl, substituted pyrrolidinyl wherein the substituent is an alkyl containing from 1 to 4 carbon atoms and substituted piperazinyl wherein the substituent is an alkyl containing from 1 to 4 carbon atoms or an alkanol wherein the alkyl moiety contains 1 to 4 carbon atoms; Y represents H, halogen or alkyl having 1 to 4 carbon atoms; and X represents H, halogen, alkyl having 1 to 4 carbon atoms and alkoxy wherein the alkyl moiety contains 1 to 4 carbon atoms; and n is the positive integer 4.

Scheme D

The compounds of the present invention as set out in formula I in which $R_1$ and $R_2$ each independently represent H or alkyl having from 1 to 8 carbon atoms or $R_1$ and $R_2$ together with N represent an azamonocyclic ring selected from the group pyrrolidinyl, piperazinyl, substituted pyrrolidinyl wherein the substituent is an alkyl containing from 1 to 4 carbon atoms and substituted piperazinyl wherein the substituent is an alkyl containing from 1 to 4 carbon atoms or an alkanol wherein the alkyl moiety contains 1 to 4 carbon atoms; Y represents H, halogen or alkyl having 1 to 4 carbon atoms; and X represents H, halogen, alkyl having 1 to 4 carbon atoms and alkoxy wherein the alkyl moiety contains 1 to 4 carbon atoms; and n is the positive integer 1 are generally prepared by the reaction sequence set out in Scheme D.

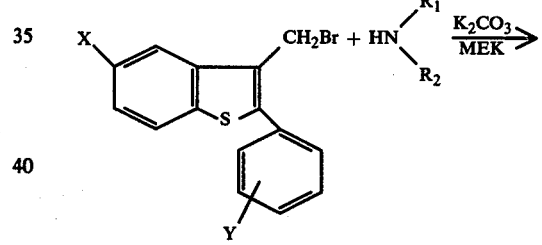

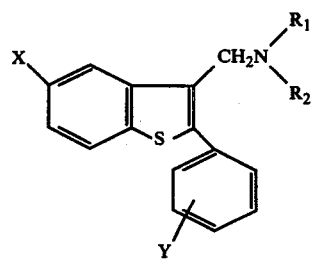

The utility of the instant compounds as neuroleptic is based on the premise that neuroleptic agents act by blocking dopamine receptors in the brain (see P. Seeman, M. Chau-Wong, J. Tedesco, and K. Wing, *Proc. Nat. Acad. Sci.*, 72, 4376 (1975) as well as references mentioned below). The support for this premise is shown by the direct effects of neuroleptic or antipsychotic drugs when tested on the stereospecific binding of [$^3$H] dopamine and of [$^3$H] haloperidol to rat or calf brain striata and their subfractions — Receptor Binding Assay. The procedure for this assay is as follows:

Calf caudate nuclei were dissected from freshly obtained brains and stored frozen at $-76°$ C. As needed, caudate tissue was homogenized and prepared following procedures outlined by Creese (see I. Creese, D. R. Burt, and S. H. Snyder, *Life Sciences*, 17 993 (1975)).

Receptor binding studies were performed as reported in the literature (I. Creese, D. R. Burt, and S. H. Snyder, *Life Sciences*, 17, 993, (1975); D. R. Burt, S. J. Enna, I. Creese, and S. H. Snyder, *Nat. Acad. Sci.*, 72, 4665 (1975); and D. R. Burt, I. Creese, and S. H. Snyder, *Mol. Pharmacol.*, 12, 800 (1976)). with slight modifications. A typical sample contained 2 ml of caudate membrane homogenate (10 mg original tissue/ml) in a final ligand concentration of either 5nM $^3$H-dopamine or 1.6nM $^3$H-Haloperidol. Test compounds were added as 20 μl aliquots from stock solutions prepared in absolute ethanol or 0.1% ascorbic acid. Samples were incubated in triplicate at 37° C. for 15 minutes when $^3$H-dopamine was used and for 10 minutes when $^3$H-Haloperidol was present.

Immediately following all incubations, proteins were recovered on Whatman GF/B glass fiber filters under reduced pressure. Trapped membranes were solubilized off the filters using 1 ml NCS tissue solubilizer (Amersham/Searle Corp.) at 50° C. for 1 hour. Then, pH was adjusted by adding 0.1 ml glacial acetic acid, 10 ml PCS (Amersham/Searle) added and samples analyzed for membrane-bound radioactivity using a Mark II liquid scintillation counter (Searle Analytical, Inc.).

Non-specific binding was measured in the presence of $10^{-5}$M (+)-Butaclamol for the $^3$H-dopamine studies, and $10^{-4}$M non-radioblabelled dopamine for the $^3$H-Haloperidol studies. IC$_{50}$ values were determined from log-probit plots using 4–6 concentrations of each compound.

A large number of neuroleptic agents were tested in this assay. Studies showed that the effectiveness (IC$_{50}$) in displacing labeled haloperidol correlated well with ED$_{50}$ doses for a number of in vivo animal tests. These included blockade of amphetamine or apomorphine stereotypic behavior in the rat, as well as apomorphine induced emesis in dogs [see I. Creese, D. R. Burt, and S. H. Snyder, *Science*, 192, 481 (1976)]. Most important is the impressive correlation of the average clinical dose to binding affinity [see P. Seeman, M. Chau-Wong, J. Tedesco, and K. Wong, *Proc. Nat. Acad. Sci.*, 72, 4376 (1975)].

There as two indications from the assay data as to whether a compound is a probable neuroleptic. Firstly, it must be a dopamine antagonist. This is determined by a higher affinity for $^3$H-Haloperidol than $^3$H-dopamine sites. In other words, it must have a high $^3$H-DA/$^3$H-HALO, IC$_{50}$ ratio.

Secondly, the absolute value for displacement of labeled haloperidol seems to correlate with the corresponding potency in vivo.

5-Chloro-2-phenylbenzo[b]thiophene-3-N,N-dimethyl ethanamine, hydrochloride; 2-phenylbenzo[b]thiophene-3-N,N-dimethylethanamine, hydrochloride; 5chloro-2-phenyl-benzo[b]thiophene-3-N,N-diethylethanamine, hydrochloride; 1-[2-(5-chloro-2-phenylbenzo[b]thiophene-3-yl)ethyl]pyrrolidine, hydrochloride; and 5-chloro-2-phenylbenzo[b]thiophene-3-N,N-dimethylpropanamine, hydrochloride as is illustrated by the following table have antagonist ratios which are comparable to clozapine and chloropromazine which are known neuroleptic agents.

| Compound | $^3$H-Dopamine | $^3$H-Haloperidol | Ratio |
| --- | --- | --- | --- |
| 5-chloro-2-phenylbenzo[b]thiophene-3-N,N-dimethylethanamine, hydrochloride | $2 \times 10^{-5}$ | $6.5 \times 10^{-7}$ | 31 |
| 2-phenylbenzo[b]thiophene-3-N,N-dimethylethanamine, hydrochloride | $1.2 \times 10^{-5}$ | $6.2 \times 10^{-7}$ | 21 |
| 5-chloro-2-phenyl-benzo[b]thiophene-3-N,N-diethylethanamine, hydrochloride | $6 \times 10^{-6}$ | $1.2 \times 10^{-7}$ | 50 |
| 1-[2-(5-chloro-2-phenyl-benzo[b]thiophene-3-yl)ethyl]pyrrolidine, hydrochloride | $4.8 \times 10^{-5}$ | $6.5 \times 10^{-7}$ | 74 |
| 5-chloro-2-phenylbenzo[b]thiophene-3-N,N-dimethylpropanamine, hydrochloride | $4.8 \times 10^{-5}$ | $3.5 \times 10^{-7}$ | 137 |
| Chloropromazine | $2.5 \times 10^{-6}$ | $3.4 \times 10^{-8}$ | 74 |
| Clozapine | $8 \times 10^{-6}$ | $1.8 \times 10^{-7}$ | 44 |
| Haloperidol | $5 \times 10^{-7}$ | $1.8 \times 10^{-9}$ | 278 |

Evidence of the anti-bacterial utility of the instant compounds vis-a-vis aerobic bacteria is provided by the following standardized test. Nutrient broth (manufactured by Baltimore Biological Laboratories) is prepared by recommended by the manufacturer, sterilized, and inoculated with Escherialla coli ATCC 8739 q.s. one million cells per ml, determined spectrophotometrically. Meanwhile, compound is heated in sterile distilled water at a concentration of 1000 mcgm per ml for 20 minutes at 80° C. This compound preparation is serially diluted and mixed with sufficient inoculated medium to afford concentrations of 100, 10, 1, and 0.1 mcgm of compound per ml. The mixtures thus obtained are incubated aerobically for 20–24 hr. at 37° C. and then examined grossly for growth of the organism. Controls are provided by concurrent incubations identical with the above except that (1) reference standards (4.3, 0.43, 0.043, and 0.0043 mcgm per ml of streptomycin sulfate and 6667, 667, 67, and 7 units of potassium penicillin G) are substituted for compound and (2) neither compound nor reference standard is present. Compounds are considered active if, at the maximum concentrations tested, no growth of organism is observed and no aberrancy is apparent in respect of the controls. Potency is expressed as the minimum concentration at which a compound is active.

5-Chloro-2-phenylbenzo[b]thiophene-3-ethanamine, hydrochloride and 1-[3-(5-chloro-2-phenylbenzo[b]thiophen-3-yl)ethyl]-4-methylpiperazine, dihydrochloride are active in the above-mentioned assay at 10 μg per ml.

5-Chloro-2-phenylbenzo[b]thiophene-3-N,N-dimethylethanamine, hydrochloride and 1-[3-(5-chloro-2-phenylbenzo-[b]thiophen-3-yl)propyl]-4-methylpiperazine, dihydrochloride, and 1-[3-(5-chloro-2-phenylbenzo[b]thiophen-3yl)methyl]-4-ethanolpiperazine, dihydrochloride are also active in the above-mentioned assay at 100 μg per ml.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees centigrade (° C.) and relative amounts of materials in parts by weight, except as otherwise noted.

EXAMPLE A

To a stirred solution of 30.6 parts by weight of p-chlorothiophenol in 200 parts by volume of pyridine is added 45.0 parts by weight of 1-bromo-1-phenyl acetone at 0° C. under a nitrogen atmosphere. The resulting solution is stirred for 1 hour at 0° C. before diluting with 150 parts by volume of 10% aqueous hydrochloric acid. The reaction mixture is then extracted with 250 parts by volume of ethyl ether. The organic phase is separated, washed (3xs) with 700 parts by volume of 10% aqueous hydrochloric acid, washed once with brine and dried over magnesium sulfate. Concentration of this solution on a rotary evaporator affords as a yellow oil p-chlorophenylthiophenylmethylmethyl ketone. This compound is represented by the following formula

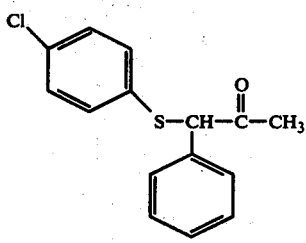

EXAMPLE B 55.7 parts by weight of p-chlorophenylthiophenylmethylmethyl ketone and 500 parts by weight polyphosphoric acid are combined in a stoppered flask and heated with stirring for 3.5 hours at 180° C. 350 Parts by volume of chlorobenzene is added to the reaction mixture and the resulting solution is heated at reflux temperature for an additional hour. After cooling the organic phase of this reaction solution is decanted off; the inorganic phase is dissolved in ice water and extracted once each with benzene and ethyl ether. The combined organic phases are then washed once with a saturated solution of sodium bicarbonate, washed once with brine, and dried over magnesium sulfate. Concentration of this solution in vacuo affords a dark solid. Crystallization of this solid (2xs) from heptane affords a brown solid. Sublimation at 135° C/0.1mm of this brown solid affords 5-chloro-3-methyl-2-phenylbenzo[b]thiophene, melting at 108.5°–110° C. This compound is represented by the following structural formula.

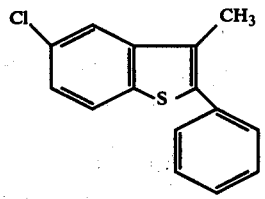

EXAMPLE C 0.5 Part by weight of 5-chloro-3-methyl-2-phenylbenzo[b]thiophene and 0.379 part by weight of N-bromosuccinimide are combined in 25 parts by volume of carbon tetrachloride with a catalytic amount of benzoyl peroxide. The resulting mixture is heated at reflux temperature for 1 hour. After cooling, the reaction mixture is filtered. Concentration of the filtrate on a rotary evaporator affords a yellow solid. Crystallization of this solid from 300 parts by volume of Skelly solvent B affords as a white solid 3-bromoethyl-5-chloro-2-phenylbenzo[b]thiophene. This compound is represented by the following structural formula.

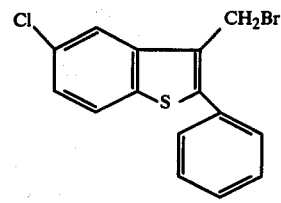

EXAMPLE D 13.0 Parts by weight of 3-bromomethyl-5-chloro-2-phenylbenzo[b]thiophene, 5.1 parts by weight of potassium cyanide and 1.5 parts by weight of potassium iodide are suspended in 250 parts by volume of 95% ethanol and heated at 52° C. under a nitrogen atmosphere for 22.5 hours. The reaction mixture is then diluted with 250 parts by volume of water and stirred for an additional 0.5 hour. The resulting precipitate is separated from the reaction mixture by filtration. Crystallization of this precipitate from ethyl acetate affords as a white crystalline solid 5-chloro-2-phenylbenzo[b]thiophene-3-acetonitrile, melting at 158°–160° C. This compound is represented by the following structural formula.

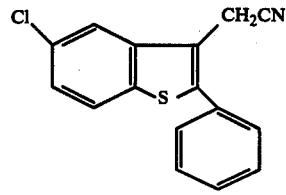

EXAMPLE E 22.2 Parts by weight of 5-chloro-2-phenylbenzo[b]thiophene-3-acetonitrile is suspended in 500 parts by volume of absolute ethanol. The resulting mixture is cooled to between 0° to −10° C. Hydrogen chloride gas is then bubbled through this cooled solution for 1 hour before allowing the solution to warm to room temperature. The mixture is then allowed to stir at room temperature for 40 hours. The resulting reddish solution is poured into 500 parts by weight of ice and then heated at 85° C. for 6 hours. After sitting overnight at room temperature the solution is diluted with an additional 1000 parts by volume of water and then extracted (3xs) with ethyl ether. The combined organic extracts are washed once each with water, saturated sodium bicarbonate solution and brine before drying over magnesium sulfate. Concentration on a rotary evaporator affords as a dark yellow oil ethyl 5-chloro-2-phenylbenzo[b]thiophene-3-acetate. This compound is represented by the following structural formula

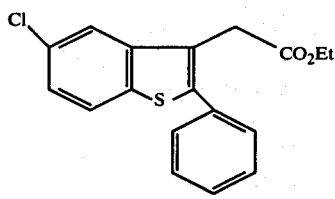

EXAMPLE F

To a suspension of 11.5 parts by weight of lithium aluminum hydride in 100 parts by volume of refluxing ethyl ether under a nitrogen atmosphere is added over a 0.25 hour addition period 25.0 parts by weight of ethyl 5-chloro-2-phenylbenzo[b]thiophene-3-acetate in 100 parts by volume of ethyl ether. The resulting mixture is heated at reflux temperature for 48 hours before cooling to 0° C. and quenching with cautious sequential addition of 11.5 parts by volume of water, 11.5 parts by volume of 15% aqueous sodium hydroxide solution and 34.5 parts by volume of water. The reaction mixture is stirred for an additional two hours at 0° C. before the granular aluminum salts are removed by vacuum filtration. The aluminum salts are then washed with a liberal amount of ethyl ether. Concentration of the filtrate in vacuo affords 5-chloro-2-phenylbenzo[b]thiophene-3-ethanol as an off-white solid material. This material is represented by the following structural formula

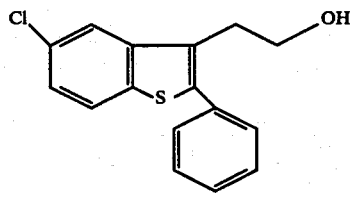

EXAMPLE G

To a cooled solution of 0.5 part by weight of 5-chloro-2-phenylbenzo[b]thiophene-3-ethanol in 10.0 parts by volume of pyridine is added 0.66 parts by weight of tosyl chloride. The reaction solution is then placed in the refrigerator for 22 hours. After the 22 hour period the reaction solution is poured into 50 parts by volume of ice water causing the product to oil out. This aqueous mixture is then extracted twice with ethyl ether. The organic layers are combined, washed (3xs) with a 1:1 aqueous hydrochloric acid-water mixture, then washed with water and dried over Na₂CO₃—Na₂SO₄. Concentration in vacuo of the organic layer affords a white solid. Crystallization of this white solid (2xs) from ethanol affords 5-chloro-2-phenylbenzo[b]-thiophene-3-ethyl-β-tosylate. This compound is represented by the following structural formula.

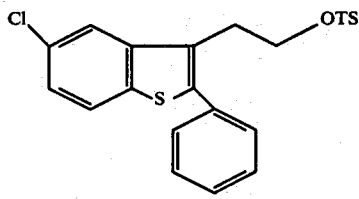

EXAMPLE H

To a cooled and stirred suspension of 3.93 parts by weight of sodium hydride in 50 parts by volume of tetrahydrofuran is added over a 30 minute addition period 26.1 parts by weight of diethyl malonate in 50 parts by volume of tetrahydrofuran. To the resultant solution is then added 50 parts by weight of 5-chloro-2-phenyl-1-benzo[b]thiophene-3-methyl bromide in 150 parts by volume of tetrahydrofuran over a 5 minute addition period. The mixture is then stirred at ambient temperature for 18 hours before the precipitated sodium bromide is removed by vacuum filtration. Concentration of the filtrate affords a white solid. Crystallization of this solid (2xs) from Skelly B affords 5-chloro-2-phenyl-1-benzo[b]thiophene-3-ethyl(2',2'-bis ethyl carboxylate), melting at 97.5–98.5° C. This compound is represented by the following structural formula.

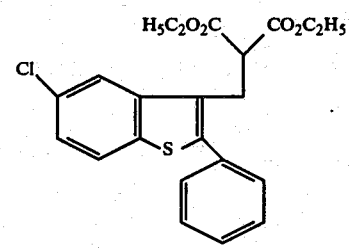

EXAMPLE I

To a suspension of 35 parts by weight of 5-chloro-2-phenyl-1-benzo[b]thiophene-3-ethyl(2',2'-bis ethyl carboxylate in methanol is added 28 parts by weight of potassium hydroxide. The resultant mixture is stirred at ambient temperature for 24 hours. A white solid potassium salt precipitates and is isolated by vacuum filtration. The methanol solution is acidified with 250 parts by volume of a 50% aqueous hydrochloric acid solution. Most of the methanol is removed and the remaining aqueous mixture is heated on a steam bath for about 30 minutes. An oil separates which after cooling is extracted with ether. The organic layer is dried with brine and magnesium sulfate and then concentrated to afford 5-chloro-2-phenyl-benzo[b]-thiophene-3-β-propionic acid as a viscous glass. This compound is represented by the following structural formula.

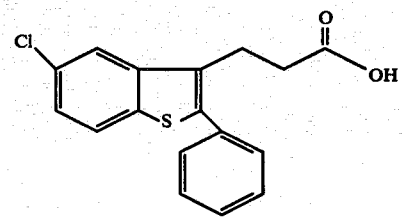

EXAMPLE J

To a suspension of 25 parts by weight of 5-chloro-2-phenyl-benzo[b]thiophene-3-β-propionic acid in 500 parts by volume of benzene is added 25 parts by weight of oxalylchloride. The resultant mixture is heated under reflux for 21 hours. The solvent and excess oxalylchloride are distilled at atmospheric pressure until a volume of 200 parts by volume remains. This material is then concentrated on a rotary evaporator. Two 100-parts by volume portions of benzene are then added to this material and subsequently concentrated to a viscous yellow oil. This oil is the acid chloride of 5-chloro-2-phenylbenzo[b]thiophene-3-β-propionic acid. Into a solution of the acid chloride in tetrahydrofuran which is cooled to 0° C. is bubbled dimethylamine. After the addition of the dimethylamine the reaction mixture is allowed to warm to room temperature and then stirred an additional 19 hours. The mixture is then partitioned between water and ether. The organic layer is separated, washed with water (3xs), washed with brine, dried over magnesium sulfate and concentrated in vacuo to yield a yellow oil. Crystallization of this oil from isopropyl alcohol affords 5-chloro-2-phenylbenzo[b]thiophene-3-β-N,N,dimethylpropionamide melting at 129–131° C. This compound is represented by the following structural formula.

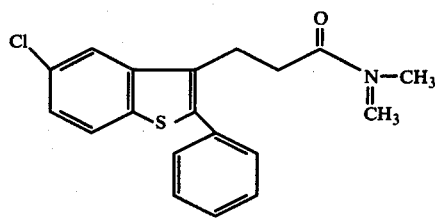

Various amines such as diethylamine, N-methylpiperazine and pyrrolidine could be substituted in the above-described procedure to obtain the respective amides.

It would be obvious to one skilled in the art of organic chemistry that Examples A to J also serve to teach the preparation of starting materials for the compounds of Formula I in which X represents H, halogen (other then chloride) alkyl having 1 to 4 carbon atoms and alkoxy wherein the alkyl moiety contains 1 to 4 carbon atoms and Y represents H, halogen and alkyl having 1 to 4 carbon atoms by substitution of the appropriate starting material.

EXAMPLE 1

To a suspension of 6.9 parts by weight of 5-chloro-2-phenylbenzo[b]thiophene-3-acetonitrile in a solution of 11.6 parts by weight of cobaltous chloride hexahydrate in 300 parts by volume of methanol-benzene (5:1) is added, slowly, 9.2 parts by weight of sodium borohydride at 0° C. After the addition is completed, the mixture is allowed to warm to room temperature and then stirred for 19 hours. To the solution is now added 100 parts by volume of 3N hydrochloric acid. The solution is then stirred an additional 2 hours. The reaction mixture is partitioned between water and ether. The aqueous layer is separated, basified with concentrated ammonium hydroxide and extracted (3xs) with ether. The organic fractions are combined, washed with brine, dried over magnesium sulfate and concentrated to afford crude 5-chloro-2-phenylbenzo[b]thiophene-3-ethaneamine as a yellow oil. This oil is dissolved in 15 parts by volume of isopropanol; to this solution is then added 8.0 parts by volume of isopropanolic/HCl. A solid precipitates out; 30 parts by volume of ethyl ether is now added and the mixture is stirred overnight. Removal by vacuum filtration of the resulting white solid material affords 5-chloro-2-phenylbenzo[b]thiophene-3-ethanamine hydrochloride, melting dec > 250° C. This compound is represented by the following structural formula

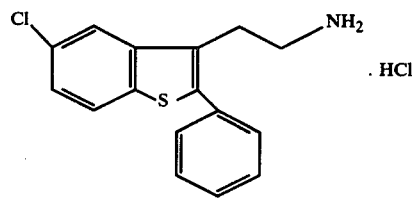

The remaining material is boiled in 7.0 parts by volume of 15% aqueous sodium hydroxide solution before adding chloroform to dissolve the oil which is formed. The chloroform layer is separated and concentrated to afford a colorless oil which solidifies upon standing under high vacuum overnight. This oil is crude 5-chloro-2-phenylbenzo[b]thiophene-3-ethanamine.

EXAMPLE 2

3.0 Parts by weight of 5-chloro-2-phenylbenzo[b]thiophene-3-ethyl-β-tosylate and 21 parts by volume of dimethylamine are mutually dissolved in 50 parts by volume of dry dimethylformamide and heated in a bomb at 68° C. for 26 hours. The reaction mixture is then poured into water and extracted with ether. The organic layer is separated, washed with water (3xs), then washed with brine, dried over magnesium sulfate and concentrated on a rotary evaporator to afford crude 5-chloro-2-phenylbenzo[b]thiophene-3-N,N-dimethylethanamine. The hydrochloride salt of this compound is formed by the slow addition of 5.0 parts by volume of isopropanolichydrochloric acid to a stirred solution of 5-chloro-2-phenylbenzo[b]thiophene-3-N,N-dimethylethanamine in 70 parts by volume of isopropyl alcohol. A floculent white solid separates from solution and after 30 minutes 70 parts by volume of ether is added to further precipitate the salt. Filtration yields, after washing with ether, 5-chloro-2-phenylbenzo[b]thiophene-3-N,N-dimethylethanamine hydrochloride, melting at 231–232° C. This compound is represented by the following structural formula.

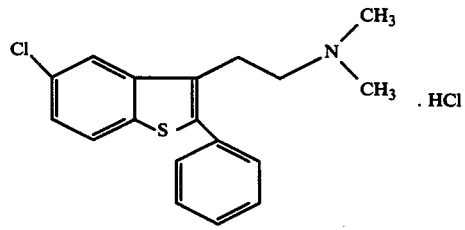

EXAMPLE 3

Substitution of an equivalent quantity of diethylamine for the dimethylamine of Example 2 and repetition of the procedure which is described in Example 2 affords 5-chloro-2-phenylbenzo[b]thiophene-3-N,N-diethylethanamine hydrochloride, melting at 178° C. This compound is represented by the following structural formula.

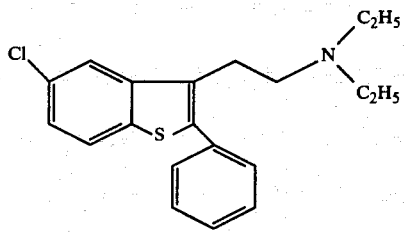

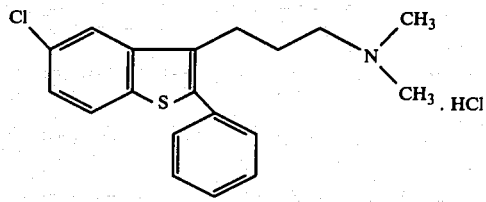

EXAMPLE 4

Dimethylamine is bubbled for 0.5 hour into a stirred solution of 13.0 parts by weight of 5-chloro-2-phenylbenzo[b]thiophene-3-β-propionyl chloride in 100 parts by volume of tetrahydrofuran cooled to 0° C. with an ice bath. After the addition of the dimethylamine is completed the mixture is allowed to warm to room temperature and stirred an additional 19 hours. The reaction mixture is partitioned between water and ether. The organic layer is separated, washed with water (3xs), then washed with brine, dried over magnesium sulfate and concentrated in vacuo to afford a yellow oil. Crystallization of this oil from isopropyl alcohol affords 5-chloro-2-phenylbenzo[b]thiophene-3-N,N-dimethyl propanamide, melting at 129–131° C. This compound is represented by the following structural formula.

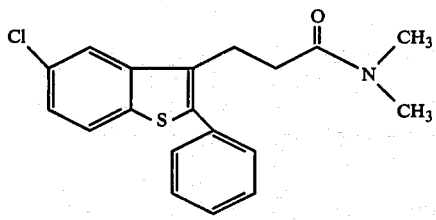

EXAMPLE 5

To a suspension of 1.0 parts by weight of lithium aluminum hydride in 25 parts by volume of refluxing ether is added dropwise a solution of 4.0 parts by weight of 5-chloro-2-phenylbenzo[b]thiophene-3-N,N-dimethyl propanamide in 25 parts by volume of ether. The reaction mixture is then heated at reflux temperature for 20 hours before it is cooled to 0° C. and quenched with the cautious sequential addition of 1 part by volume of water, 1 part by volume of 15% aqueous solution of sodium hydroxide and 3 parts by volume of water. The reaction mixture is stirred an additional 0.5 hour before the granular aluminum salts are removed by vacuum filtration and then washed liberally with ether. Concentration of the filtrate affords a colorless oil which is crude 5-chloro-2-phenylbenzo[b]thiophene-3-N,N-dimethyl propanamine. This oil is dissolved in 100 parts by volume of isopropanol before adding 8 parts by volume of isopropanolic/HCl. A white solid precipitates from the solution and after 0.25 hour, 150 parts by volume of ether is added. The white solid is isolated by filtration and washed with ether to afford 5-chloro-2-phenylbenzo[b]thiophene-3-N,N-dimethylpropanamine hydrochloride melting at 252–253.5° C. This compound is represented by the following structural formula.

EXAMPLE 6

3.0 Parts by weight of 5-chloro-2-phenylbenzo[b]thiophene-3-ethyl-β-tosylate and 3.0 parts by weight of methyl piperazine are mutually dissolved in 22 parts by weight of dry dimethylformamide and heated at 100° C. under a nitrogen atmosphere for 3 hours. The reaction mixture is then poured into water and extracted with ether. The organic layer is separated, washed with water (3xs), washed with brine, dried over magnesium sulfate and concentrated in vacuo to afford as an orangish oil crude 1-[3-(5-chloro-2-phenylbenzo[b]thiophene-3-yl)ethyl]-4-methylpiperazine. The hydrochloride salt is formed by the slow addition of 5.0 parts by volume of isopropanolic/HCl to a stirred solution of crude 1-[3-(5-chloro-2-phenylbenzo[b]thiophen-3-yl)ethyl]-4-methylpiperazine in 50 parts by volume of isopropanol. After the addition of the isopropanolic/HCl is completed, the reaction mixture is further diluted with 50 parts by volume of ether. Filtration affords as a white solid, which is washed 3xs with ether, 1-[3-(5-chloro-2-phenylbenzo[b]thiophen-3-yl)ethyl]-4-methylpiperazine dihydrochoride, melting 250° C. dec. slowly. This compound is represented by the following structural formula.

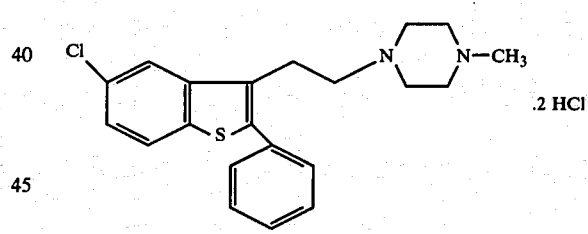

EXAMPLE 7

Substitution of an equivalent quantity of methylamine for the methylpiperazine of Example 6 and repetition of the procedure which is described in Example 6 affords 5-chloro-2-phenylbenzo[b]thiophene-3-N-methylethanamine hydrochloride, melting at 212° C. (dec). This compound is represented by the following structural formula.

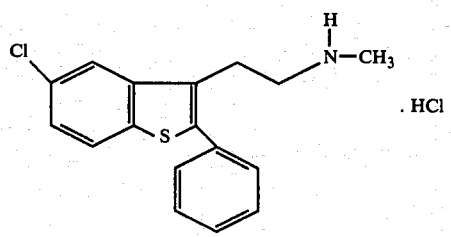

EXAMPLE 8

To a stirred suspension of 2.5 parts by weight of lithium aluminum hydride in 50 parts by volume of tetrahydrofuran is added slowly 4.0 parts by weight of

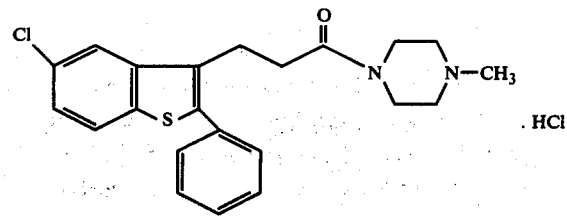

The resulting mixture is heated at reflux for 18 hours before it is cooled to 0° C. and quenched with the cautious sequential addition of 2.5 parts by volume of water, 2.5 parts by volume of 15% aqueous sodium hydroxide solution and 7.5 parts by volume of water. The granular aluminum salts are then removed from the reaction mixture by filtration and washed well with ether. Concentration of the filtrate in vacuo affords a colorless oil which is 1-[3-(5-chloro-2-phenylbenzo[b]thiophen-3-yl)propyl]-4-methylpiperazine. This material is now dissolved in 60 parts by volume of isopropanol before slowly adding 10 parts by volume is isopropanol/HCl (0.27g/ml). A white solid precipitates and 400 parts by volume of ether is added. The resultant salt is isolated by filtration and washed with ether. This material is 1-[3-(5-chloro-2-phenylbenzo[b]thiophen-3-yl)propyl]-4-methylpiperazine dihydrochloride melting at 239°–240° C. The compound is represented by the following structural formula.

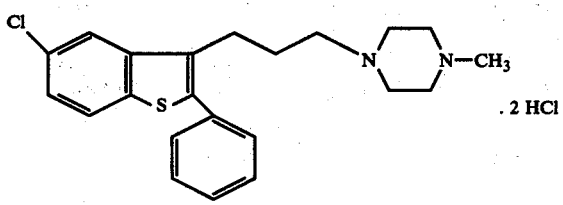

EXAMPLE 9

To a suspension of 15.5 parts by weight of 2-phenylbenzo[b]thiophene-3-acetonitrile in a solution of 29.6 parts by weight of cobaltous chloride hexahydrate in 769 parts by volume of methanol-benzene (5:1) is added slowly 23.8 parts by weight of sodium borohydride at 0° C. After the addition is completed, the mixture is allowed to warm to room temperature and stirred for 72 hours. The reaction mixture is then partitioned between water and ether. The aqueous layer is separated, basified with concentrated ammonium hydroxide and extracted (3xs) with ether. The organic fractions are combined, dried and concentrated to afford crude 2-phenylbenzo[b]thiophene-3-ethanamine. This material is dissolved in chloroform and shaken with 100 parts by volume of 10% aqueous hydrochloric acid. A solid precipitates; filtration of this material affords 2-phenylbenzo[b]thiophene-3-ethanamine hydrochloride, melting at 200°–201° C. (decomposition). This compound is represented by the following stuctural formula.

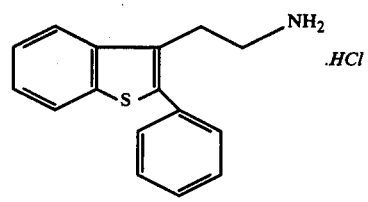

EXAMPLE 10

Substitution of an equivalent quantity of 5-fluoro-2-phenylbenzo[b]thiophene-3-acetonitrile for the 2-phenylbenzo[b]thiophene-3-acetonitrile of Example 9 and repetition of the procedure which is described in Example 9 affords 5-fluoro-2-phenylbenzo[b]thiophene-3-ethanamine hydrochloride, melting at 260° C. (decomposition). This compound is represented by the following structural formula.

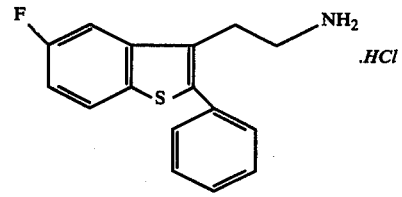

EXAMPLE 11

To a solution of 0.9 part by weight of 5-fluoro-2-phenylbenzo[b]thiophene-3-ethanamine hydrochloride in 7.0 parts by volume of 90% aqueous formic acid is added 0.7 part by volume of 37% aqueous formaldehyde. The resulting mixture is heated at 70° C. in a nitrogen atmosphere for 15 hours and then heated at 100° C. for 8 hours. The mixture is then partitioned between 10% aqueous hydrochloric acid and ether. The aqueous layer is separated; this layer is then basified with 50% aqueous sodium hydroxide solution with cooling and extracted with benzene (3xs). The combined benzene extracts are dried and concentrated to afford as a yellow oil 5-fluoro-2-phenylbenzo[b]thiophene-3-N,N-dimethyl ethanamine hydrochloride. This compound is represented by the following structural formula.

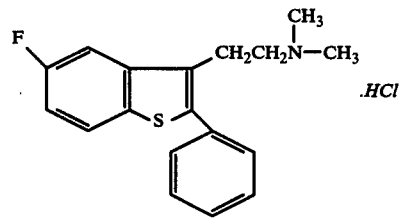

EXAMPLE 12

Substitution of an equivalent quantity of 2-phenylbenzo[b]thiophene-3-ethanamine hydrochloride for the 5-fluoro-2-phenylbenzo[b]thiophene-3-ethanamine hydrochloride of Example 11 and repetition of the procedure which is described in Example 11 affords 2-phenylbenzo[b]thiophene-3-N,N-dimethylethanamine hydrochloride. This compound is represented by the following structural formula.

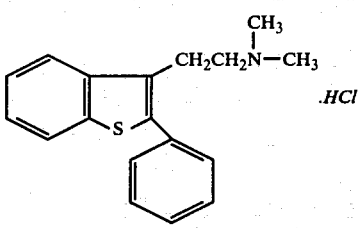

EXAMPLE 13

2.0 Parts by weight of 5-chloro-2-phenylbenzo[b]thiophene-3-ethyl-β-tosylate and 20 parts by volume of dibutylamine are combined and refluxed over the weekend. The reaction mixture is then poured into water and extracted with ethyl acetate. The organic layer is separated, washed (2xs) with water, then washed with sodium carbonate solution and dried over magnesium sulfate. The dried solution is then concentrated on a rotary evaporator to afford crude 5-chloro-2-phenylbenzo[b]thiophene-3-N,N-dibutylethanamine. Substitution of 5-chloro-2phenylbenzo[b]thiophene-3-N,N-dibutylethanamine for the 5-chloro-2-phenylbenzo[b]thiophene-3-N,N-dimethyl ethanamine of Example 2 and repetition of the procedure of Example 2 for the formation of the hydrochloride salt affords 5-chloro-2-phenylbenzo[b]thiophene-3-N,N-dibutylethanamine hydrochloride, melting at 176°–177° C. The compound is represented by the following structural formula

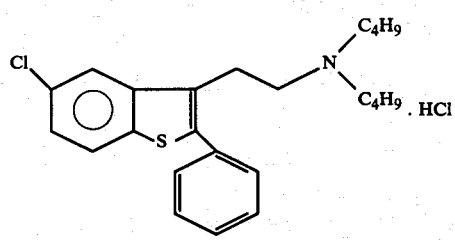

EXAMPLE 14

0.45 Part by weight of dimethylamine is condensed into a cooled (5° C.) suspension of 3.0 parts by weight of anhydrous potassium carbonate in 120 parts by volume of methyl ethyl ketone. To this reaction mixture is now added 5.0 parts by weight of 3-bromomethyl-2-phenylbenzo[b]thiophene in 120 parts by volume of methyl ethyl ketone. This mixture is stirred at 5° C. for 2 hours and then at ambient temperature overnight. The reaction mixture is filtered and the filtrate is concentrated to afford an oil. The residual oil is diluted with ethyl ether, washed (2xs) with water, washed with a saturated solution of sodium chloride and dried over magnesium sulfate. The dried solution is concentrated in vacuo to afford material which is crystallized from isopropyl alcohol to yield 2-phenylbenzo[b]thiophene-3-N,N-dimethylmethanamine. Substitution of 2-phenylbenzo[b]thiophene-3-N,N-dimethylmethanamine for the 5-chloro-2-phenylbenzo[b]thiophene-3-N,N-dimethylethanamine of Example 2 and repetition of the procedure of Example 2 for the formation of the hydrochloride salt affords 2-phenylbenzo[b]thiophene-3-N,N-dimethylmethananamine hydrochloride, melting at 231°–235° C. This compound is represented by the following structural formula.

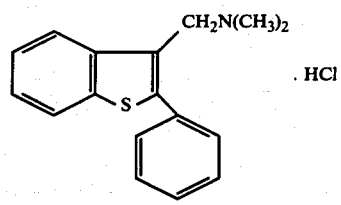

EXAMPLE 15

Substitution of an equivalent quantity of 3-bromomethyl-5-chloro-2-phenylbenzo[b]thiophene for the 3-bromomethyl-2-phenylbenzo[b]thiophene of Example 14 and repetition of the procedure which is described affords 5-chloro-2-phenylbenzo[b]thiophene-N,N-dimethylmethanamine hydrochloride, melting at 114°–115° C. The compound is represented by the following structural formula.

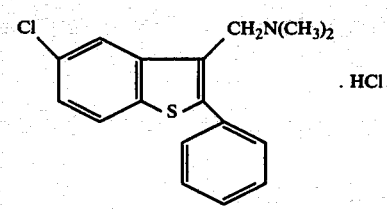

EXAMPLE 16

Substitution of an equivalent quantity of N-methylpiperazine for the dimethylamine of Example 14 and following the procedure of Example 14 affords 1-[(2-phenylbenzo[b]thiophen-3-yl)methyl]-4-methylpiperazine dihydrochloride, melting at 255°–257° C. This compound is represented by the following structural formula.

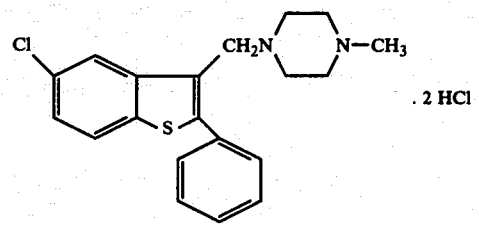

EXAMPLE 17

Substitution of an equivalent quantity of N-β-hydroxyethylpiperazine for the N-methyl piperazine of Example 16 and repetition of the procedure which is described in Example 16 affords 1-[(5-chloro-2-phenylbenzo[b]thiophen-3-yl)methyl]-4-ethanol piperazine dihydrochloride melting at 225°–237° C. This compound is represented by the following structural formula.

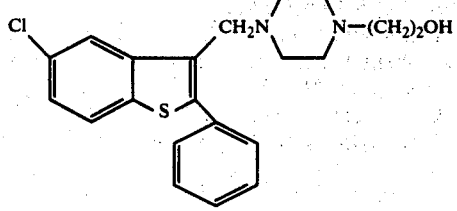

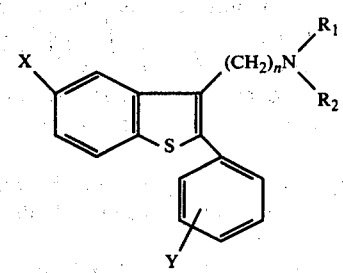

EXAMPLE 18

Substitution of an equivalent quantity of pyrrolidine for the N-methyl piperazine of Example 6 and repetition of the procedure which is described in Example 6 affords 1[2-(5-chloro-2-phenylbenzo[b]thiophen-3-yl)ethyl]pyrrolidine hydrochloride, melting at 170°–175° C. This compound is represented by the following structural formula.

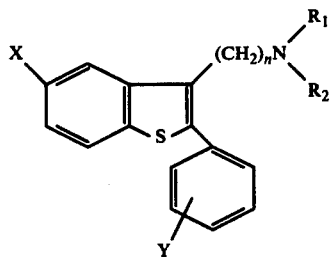

What is claimed is:

1. A compound of the formula

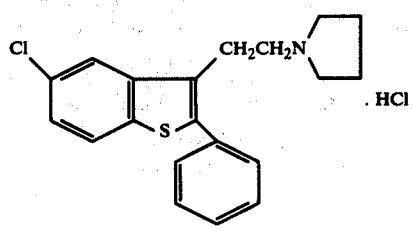

and the pharmaceutically acceptable acid addition salts wherein $R_1$ and $R_2$ each independently represents H or alkyl having from 1 to 8 carbon atoms or $R_1$ and $R_2$ together with N reresent an azamonocyclic ring selected from the group consisting of pyrrolidinyl, piperazinyl, substituted pyrrolidinyl wherein the substituent is alkyl containing from 1 to 4 carbon atoms and substituted piperazinyl wherein the substituent is alkyl containing from 1 to 4 carbon atoms or hydroxy alkyl wherein the alkyl moiety contains 1 to 4 carbon atoms; Y represents H, halogen or alkyl having 1 to 4 carbon atoms; X represents H, halogen, alkyl having 1 to 4 carbon atoms and alkoxy wherein the alkyl moiety contains 1 to 4 carbon atoms; and n is a positive integer from 1 to 4.

2. A compound according to claim 1 of the formula and the pharmaceutically acceptable acid addition salts wherein $R_1$ and $R_2$ each independently represents H or alkyl having from 1 to 8 carbon atoms; Y represents H, halogen and alkyl having 1 to 4 carbon atoms; X represents H, halogen, alkyl having 1 to 4 carbon atoms and alkoxy wherein the alkyl moiety contains 1 to 4 carbon atoms; and n is a positive integer from 1 to 4.

3. A compound according to claim 1 of the formula and the pharmaceutically acceptable acid addition salts wherein $R_1$ and $R_2$ together with N represents an azamonocyclic ring selected from the group consisting of pyrrolidinyl, piperazinyl, substituted pyrrolidinyl wherein the substituent is alkyl containing from 1 to 4 carbon atoms and substituted piperazinyl wherein the substituent is alkyl containing from 1 to 4 carbon atoms or hydroxy alkyl wherein the alkyl moiety contains 1 to 4 carbon atoms; Y represents H, halogen and alkyl having 1 to 4 carbon atoms; X represents H, halogen, alkyl having 1 to 4 carbon atoms and alkoxy wherein the alkyl moiety contains 1 to 4 carbon atoms; and n is a positive integer from 1 to 4.

4. A compound according to claim 1 of the formula

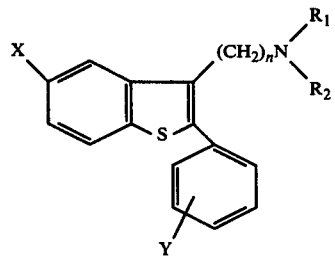

and the pharmaceutically acceptable acid addition salts wherein $R_1$ and $R_2$ each independently represents H or alkyl having from 1 to 8 carbon atoms or $R_1$ and $R_2$ together with N represent an azamonocyclic ring selected from the group consisting of pyrrolidinyl, piperazinyl, substituted pyrrolidinyl wherein the substituent is alkyl containing from 1 to 4 carbon atoms and substituted piperazinyl wherein the substituent is alkyl containing from 1 to 4 carbon atoms or hydroxy alkyl wherein the alkyl moiety contains 1 to 4 carbon atoms; Y represents H, halogen or alkyl having 1 to 4 carbon atoms; X represents H, halogen, alkyl having 1 to 4 carbon atoms and alkoxy wherein the alkyl moiety contains 1 to 4 carbon atoms; and n is a positive integer 2.

5. A compound according to claim 1 which is 1-[2-(5chloro-2-phenylbenzo[b]thiophen-3-yl)ethyl]pyrrolidene, hydrochloride.

6. A compound according to claim 1 which is 1-[3-(5-chloro-2-phenylbenzo[b]thiophen-3-yl)propyl]-4-methylpiperazine, dihydrochloride.

7. A compound according to claim 1 which is 1-[3-(5-chloro-2phenylbenzo[b]thiophen-3-yl)ethyl]-4-methyl-piperazine, dihydrochloride.

8. A compound according to claim 1 which is 1-[2-(5-chloro-2-phenylbenzo[b]thiophen-3-yl)methyl]-4-ethanol piperazine, dihydrochloride.

9. A compound according to claim 1 which is 1-[3-(5-chloro-2-phenylbenzo[b]thiophen-3-yl)methyl]-4-methylpiperazine, dihydrochloride.

10. A compound according to claim 1 which is 5-chloro-2-phenylbenzo[b]thiophene-3-ethanamine, hydrochloride.

11. A compound according to claim 1 which is 5-chloro-2-phenylbenzo[b]thiophene-3-N,N-dimethylethanamine, hydrochloride.

12. A compound according to claim 1 which is 5-chloro-2-phenylbenzo[b]thiophene-3-N,N-dimethylpropanamine, hydrochloride.

13. A compound according to claim 1 which is 5-chloro-2-phenylbenzo[b]thiophene-3-N,N-diethylethanamine, hydrochloride.

14. A compound according to claim 1 which is 5-chloro-2-phenylbenzo[b]thiophene-3-N-methylethanamine, hydrochloride.

15. A compound according to claim 1 which is 5-chloro-b 2phenyl-1-benzo[b]thiophene-N,N-dimethylmethanamine.

16. A compound according to claim 1 which is 5-fluoro-2-phenylbenzo[b]thiophene-3-ethanamine, hydrochloride.

17. A compound according to claim 1 which is 5-chloro-2-phenylbenzo[b]thiophene-3-N,N-dibutylethanamine, hydrochloride.

18. A compound according to claim 1 which is 5-fluoro-2-phenylbenzo[b]thiophene-3-N,N-dimethylethanamine, hydrochloride.

19. A compound according to claim 1 which is 2-phenylbenzo[b]thiophene-3ethanamine, hydrochloride.

20. A compound according to claim 1 which is 2-phenylbenzo[b]thiophene-3-N,N-dimethylethanamine, hydrochloride.

21. A compound according to claim 1 which is 2-phenylbenzo[b]thiophene-N,N-dimethylmethanamine, hydrochloride.

* * * * *